United States Patent [19]

Watanabe et al.

[11] 4,295,042

[45] Oct. 13, 1981

[54] METHOD OF AND DEVICE FOR MEASURING CHLOROPHYLL OF LIVING LEAVES

[75] Inventors: Shigeru Watanabe, Tokyo; Tatsuo Kuzunuki, Minami-ashigara, both of Japan

[73] Assignee: Fuji Photo Film Co. Ltd., Minamiashigara, Japan

[21] Appl. No.: 76,475

[22] Filed: Sep. 17, 1979

[30] Foreign Application Priority Data

Sep. 18, 1978 [JP] Japan .................................. 53/114364

[51] Int. Cl.³ ............................................... G01J 3/34
[52] U.S. Cl. ..................................... 250/226; 356/320
[58] Field of Search ................ 250/226; 356/320, 407; 209/576, 577, 580, 588

[56] References Cited

U.S. PATENT DOCUMENTS 3,821,550  6/1974  Priest .................................. 250/226
3,910,710  10/1975  Henderson et al. .............. 356/73 X Primary Examiner—David C. Nelms
Assistant Examiner—Darwin R. Hostetter

[57] ABSTRACT

In a method for measuring chlorophyll of a leaf of a plant, the light having passed through the leaf is divided into a light component of a shorter wavelength the amount of which changes with the amount of chlorophyll and another component of a longer wavelength the amount of which does not change with the amount of chlorophyll. The amount of these two components are measured at the same time and the difference therebetween is used for determining the amount of chlorophyll contained in the leaf. A chlorophyll meter utilizing the method is provided with a spectroscopic dividing means for dividing the light which has passed through the leaf into the two components.

6 Claims, 7 Drawing Figures

METHOD OF AND DEVICE FOR MEASURING CHLOROPHYLL OF LIVING LEAVES

BACKGROUND OF THE INVENTION

1. Field of the Invention

This invention relates to a method for measuring the amount of chlorophyll and also to a chlorophyll meter, and more particularly to a method of optically measuring the amount of chlorophyll of living leaves and a meter for measuring the same.

2. Description of the Prior Art

It is known in the art that the spectroscopic absorption shows the maximum absorption at about 670 nm and the constant minimum absorption in the range over 750 nm. The maximum absorption is caused by absorption by chlorophyll and the minimum absorption has nothing to do with chlorophyll.

By utilizing the spectoscopic absorption as above, it is known to measure the amount of chlorophyll contained in the leaves. It is mentioned in Proceedings of the Corp Science Society of Japan, Vol. 17, pages 158-162.

The conventional chlorophyll meter disclosed in the above document is provided with two interference filters having the principal wavelength of 670 nm and 750 nm, respectively. This meter first measures the light passing through the leaves through the interference filter of the principal wavelength of 750 nm to obtain the long wavelength region light by use of a CdS photodetector and sets the meter at zero point with the output of the photodetector obtained at this stage. Then, the filter is changed to the other one having the principal wavelength of 670 nm to measure the light passing through the leaves by use of the CdS photodetector. The output of the photodetector obtained at this stage is displayed by the meter to indicate the amount of chlorophyll of the leaves to be measured.

The above mentioned chlorophyll meter is advantageous in that the amount of chlorophyll can be measured by comparing the maximum transmission density and the minimum transmission density of the living leaves. However, it is disadvantageous in that the transmission density or the amount of light passing through the leaves must be measured twice, which results in a long measuring time and troublesome handling of the interference filters to be changed and also a complicated circuitry to measure the two outputs and compare the same.

SUMMARY OF THE INVENTION

The primary object of the present invention is to provide, therefore, a method of measuring the chlorophyll of living leaves quickly and easily.

Another object of the present invention is to provide a method of measuring the chlorophyll of living leaves which can be carried out by use of a simple device.

A further object of the present invention is, therefore, to provide a chlorophyll meter which can easily be manufactured.

The present invention is characterized in that the light passing through the leaves is divided into a short wavelength component the amount of which changes as the amount of chlorophyll changes and a long wavelength component the amount of which does not change with the amount of chlorophyll, and the amount of light of these components are measured at the same time.

The method of measuring the chlorophyll of living leaves in accordance with the present invention comprises the steps of having light from a light source pass through a leaf of a plant, dividing the light having passed through the leaf into the first component of a shorter wavelength the amount of which changes with the amount of chlorophyll and the second component of a longer wavelength the amount of which does not change with the amount of chlorophyll, and measuring the amount of both the components at the same time to know or display the amount of chlorophyll contained in the leaf.

The meter for measuring the chlorophyll of a leaf of a plant in accordance with the present invention comprises a sample holder for holding a sample of a leaf of a plant the chlorophyll of which is to be measured, a light source for generating light to pass through the leaf held by said sample holder, a spectroscopic light dividing means for dividing the light having passed through the leaf into the first component of a shorter wavelength the amount of which changes with the amount of chlorophyll and the second component of a longer wavelength the amount of which does not change with the amount of chlorophyll, two photosensors having different spectroscopic sensitivities for measuring the amount of said two components at the same time separately, and an electrical circuitry for giving an output indicative of the amount of chlorophyll contained in said sample of a leaf based on the difference between the outputs of said two photosensors, at least one of the limit of the shorter wavelength of said second light component and the limit of the longer wavelength of said first light component being determined by a spectroscopic optical element, and the other limit being determined by the spectroscopic property of said photosensor.

DESCRIPTION OF THE PREFERRED EMBODIMENTS

Figure 1:
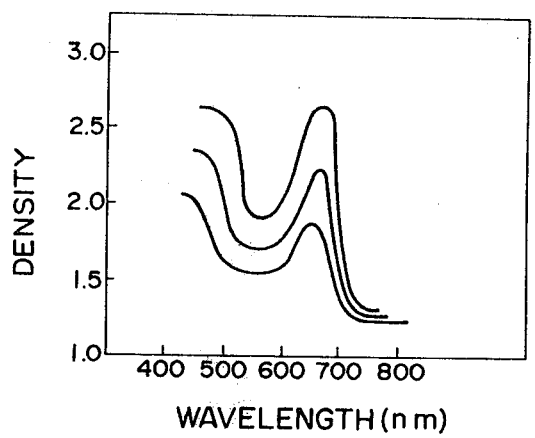
FIG. 1 is a graphical representation showing the relationship between the wavelength of the light passing through leaves of a plant and the transmission density thereof.

Referring to FIG. 1, the transmission density of a leaf of a plant has a peak at about 670 nm and a constant low region in the range over 760 nm.

Figure 2:
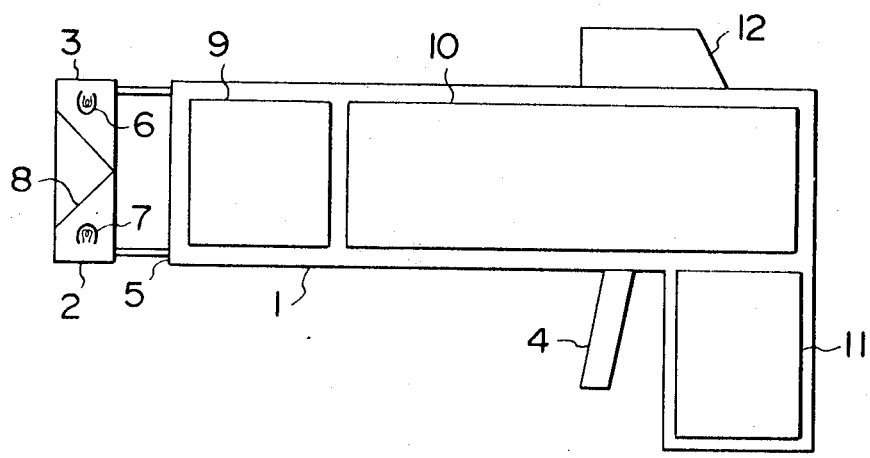
FIG. 2 is a side view of a chlorophyll meter in accordance with an embodiment of the present invention.

Referring to FIG. 2, an embodiment of the meter for measuring the chlorophyll in accordance with the present invention has a handy shape like a pistol so as to be easily handled with a hand. The body of the meter indicated by the reference numeral 1 has a casing 3 retaining therein a light source 2 at the front end thereof. The casing 3 is movable from and to the body 1 by operating a trigger 4. The casing 3 functions as a sample holder for holding a sample of a leaf when it is brought into contact with the front end of the body 1 by the operation of the trigger 4. The light source 2 is provided with a pair of lamps 6 and 7 like a tungsten lamp oppositely disposed with a mirror 8 interposed therebetween for effectively causing the light from the lamps 6 and 7 to impinge upon the sample of the leaf held between the casing 3 and the front face 5 of the body 1.

In the front part of the body 1 is provided a light receiving section 9 for receiving the light passing through the leaf held between the casing 3 and the front face 5 of the body 1. As will be described in detail hereinafter, the light having passed through the leaf is divided into the first component of a shorter wavelength the amount of which changes with the amount of chlorophyll and the second component of a longer wavelength the amount of which does not change with the amount of chlorophyll, and the amount of the two components is measured at the same time at this light receiving section 9. Behind the light receiving section 9 is provided a circuitry section 10 for determining the amount of the chlorophyll of the sample leaf based on the output of the light receiving section 9.

The pistol type body 1 has a grip portion 11 retaining therein a power source for driving the light source 2 and the circuitry provided with a power switch button. Further, on the rear upper face of the body 1 is provided with a display section 12 for displaying the amount of chlorophyll measured at the circuitry section 10 preferably in a digital form.

Now the light receiving section 9 will be described in detail referring to FIG. 3. The light receiving section 9 is enclosed by a casing 13 which is provided with apertures 14, 15 and 16 respectively on the front, rear and bottom faces thereof. The front aperture 14 is used for introducing the light from the leaf indicated at 17 held between the light source 2 and the light receiving section 9 into the interior of the casing 13. At the rear aperture 15 and the bottom aperture 16 are provided sharp cut filters 18 and 19, and photosensors 20 and 21, respectively as shown in the drawing. Among the sharp cut filters 18 and 19 and the photosensors 20 and 21, the sharp cut filter 18 and the photosensor 20 are used for measuring the amount of light component of the shorter wavelength the amount of which changes with the amount of chlorophyll, and the sharp cut filter 19 and the photosensor 21 are used for measuring the amount of light component of the longer wavelength the amount of which does not change with the amount of chlorophyll. A semi-transparent mirror 22 is provided in the casing 13 at 45° with respect to the light coming into the casing 13 through the front aperture 14 for dividing the light into the one directed to the rear aperture 15 and the other directed to the bottom aperture 16. The sharp cut filter 18 and the photosensor 20 are positioned on the optical axis of the light passing through the mirror 22 and the other filter 19 and the photosensor 21 are positioned on the optical axis of the light reflected by the mirror 22.

Figure 4:
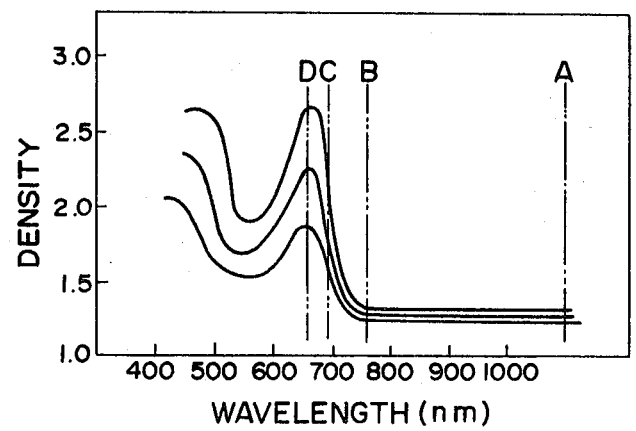
FIG. 4 is a graph showing the spectroscopic property of a spectroscopic optical element used in the meter as shown in FIG. 3.

Now the function of the sharp cut filters 18 and 19 and the photosensors 20 and 21 will be described with reference to FIG. 4. In this invention the light component of the longer wavelength has a spectroscopic distribution of 760 to 1100 nm and the light component of the shorter wavelength has a spectroscopic distribution of 660 to 690 nm. Thus, the light components have a somewhat broad range in order to provide a sufficient amount of light to effectively and accurately measure the chlorophyll.

The sharp cut filter 18 for the shorter wavelength component is used to limit the shorter limit D of the shorter wavelength region and has a spectroscopic property to only pass the light of or over 660 nm. The longer limit C of the shorter wavelength region is determined by the spectroscopic property of the photosensor 20 which is for instance a GaAsP type photodiode having relative sensitivity of about 5% for the light of 680 nm. Thus, the amount of light component having the wavelength in the region between C and D in FIG. 4 is measured by the photosensor 20.

On the other hand, the sharp cut filter 19 is used for determining the shorter limit B of the longer wavelength component. The sharp cut filter 19 has, therefore, spectroscopic property of only passing the light of or over 760 nm for example. The longer limit A of the longer wavelength component is determined by the spectroscopic property of the photosensor 21 similarly to the case of the shorter wavelength component. The photosensor 21, therefore, is for instance a silicon photodiode having relative sensitivity of about 5% for the light of 1050 nm. This, the amount of light component having the wavelength in the region between A and B in FIG. 4 is measured by the photosensor 21.

The operation of the electrical circuitry for determining the amount of chlorophyll will hereinbelow be described in detail with reference to FIG. 3 in which the output of the photosensor 21 measuring the longer wavelength component is represented by "x" and the output of the photosensor 20 measuring the shorter wavelength component is represented by "y". The output x and y are input into the dividing circuit 23 to give a value of y/x. The output y/x of the dividing circuit 23 is input into a log-conversion circuit 24 to give a value of log(y/x). Since log(y/x)=log y−log x, the output of the log conversion circuit 24 corresponds to the amount of chlorophyll contained in the leaf. In other words, the amount of chlorophyll is directly measured based on the difference between the amount of light transmission of the longer wavelength component and the amount of light transmission of the shorter wavelength component. The dividing circuit 23 is included in the electrical circuitry 10 shown in FIG. 1 together with the log-conversion circuit 24.

The output of the log-conversion circuit 24 is connected with a display section 12 to display a value corresponding to log(y/x). By the displayed value, the operator is able to know the amount of chlorophyll contained in the leaf.

Figure 3:
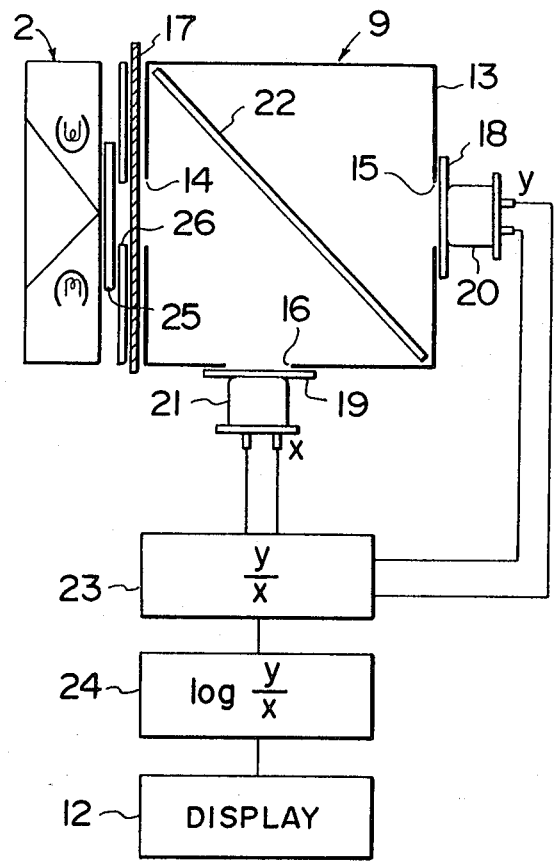
FIG. 3 is a schematic view showing the structure of a chlorophyll meter in accordance with an embodiment of the present invention.

As shown in FIG. 3, it is preferred that a light scattering plate 25 and an aperture plate 26 be provided between the leaf 17 and the light source 2.

Figure 5:
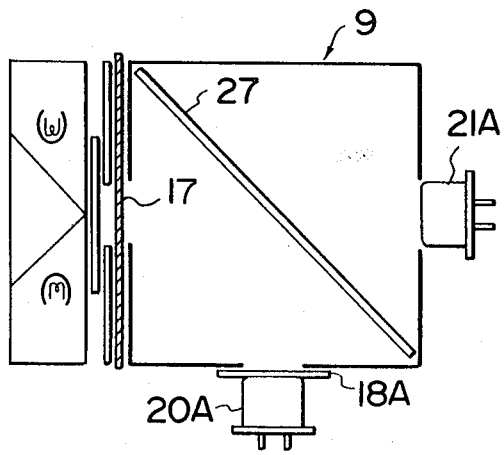
FIG. 5 is a side sectional view showing a different example of a light receiving section of the chlorophyll meter in accordance with another embodiment of the present invention.
Figure 6:
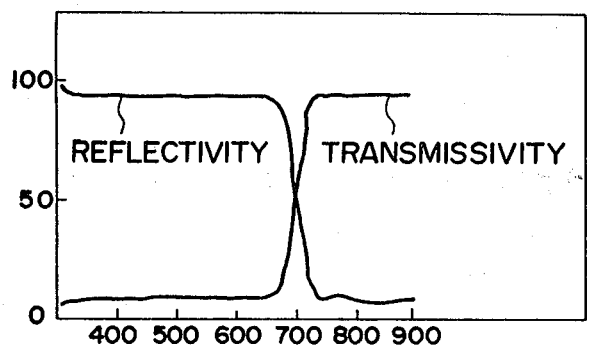
FIG. 6 is a graph showing the spectroscopic property of a dichroic filter used in the light receiving section shown in FIG. 5.

Now another embodiment of the light receiving section 9 will be described with reference to FIG. 5. In this embodiment, a dichroic filter mirror 27 is used in place of the semi-transparent mirror 22 used in FIG. 3. The dichroic filter mirror 27 has a spectroscopic property as shown in FIG. 6. The relfected light is directed to the photosensor 20A and the transmitting light is directed to the photosensor 21A. Only by the spectroscopic property, the shorter limit of the longer wavelength component and the longer limit of the shorter wavelength component are determined. Therefore, there is no need to use a sharp cut filter in front of the photosensor 21A for measuring the amount of longer wavelength component. Only in front of the photosensor 20A for measuring the shorter wavelength component is provided a sharp cut filter 18A for limiting the shorter limit of the shorter wavelength region.

Figure 7:
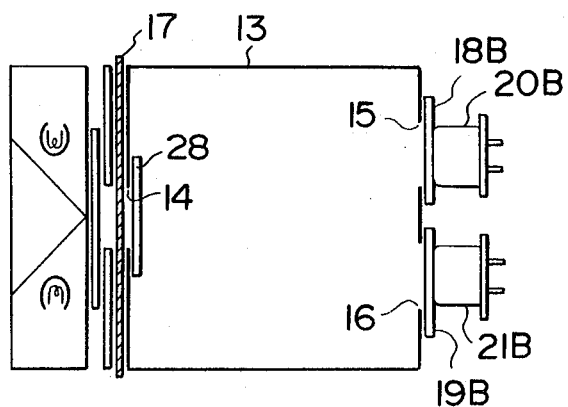
FIG. 7 is a side sectional view showing a further example of a light receiving section of the chlorophyll meter in accordance with a further embodiment of the present invention.

Another embodiment of the present invention will be described in detail with reference to FIG. 7. In this embodiment, a pair of sets of sharp cut filters 18B,19B and photosensors 20B,21B are provided on the rear end of the casing 13 in side by side relationship. The apertures 15 and 16 are also provided on the rear face of the casing 13. A light diffusion plate 28 is provided behind the front aperture 14 of the casing 13 to diffuse the light having passed through the leaf 17 so that the light may be effectively received by both the photosensors 20B and 21B. With this arrangement, there is no need to use a semi-transparent miror or a dichroic mirror in the casing 13. Accordingly, the structure is made simple and it is easy to manufacture the chlorophyll meter.

In accordance with the present invention, the mesurement of the chlorophyll can be conducted very easily and very quickly. Further, since the measurement of the two light components is conducted at the same time, there is no fear of making errors in measurement caused by aging of the sample leaf through which the light is transmitted. In addition, since the light components have sufficiently large wavelength regions and accordingly the amount of light is comparatively large, it is possible to measure the chlorophyll of a leaf having comparatively high transmission density of about 2.0 for instance.

We claim:

1. A method for measuring the amount of chlorophyll contained in a leaf of a plant comprising the steps of causing light from a light source to pass through a leaf of a plant, dividing the light which has passed through the leaf into the first component of a shorter wavelength the amount of which changes with the amount of chlorophyll contained in the leaf and the second component of a longer wavelength the amount of which does not change with the amount of chlorophyll contained in the leaf, and measuring the amount of both the components at the same time to determined the amount of chlorophyll contained in the leaf based on the difference between said amount of both the components.

2. A method as defined in claim 1 wherein said first component has a spectroscopic distribution ranging from 660 to 690 nm, and said second component has a spectroscopic distribution ranging from 760 to 1100 nm.

3. A meter for measuring the chlorophyll of a leaf of a plant comprising a sample holder for holding a sample of a leaf of a plant, a light source for generating light to pass through the leaf held by said sample holder, a spectroscopic light dividing means for dividing the light which has passed through the leaf into the first component of a shorter wavelength the amount of which changes with the amount of chlorophyll contained in the leaf and the second component of a longer wavelength the amount of which does not change with the amount of chlorophyll contained in the leaf, two photosensors having different spectroscopic sensitivities for measuring the amount of said two components at the same time separately, and an electrical circuitry for determining the amount of chlorophyll contained in the leaf based on the difference between the outputs of said two photosensors, at least one of the longer limit and the shorter limit of the spectroscopic distribution of said first and second components being determined by use of a spectroscopic optical element, and the other limit being determined by the spectroscopic property of said photosensors.

4. A meter for measuring the chlorophyll as defined in claim 3 wherein said spectroscopic optical element is two cut filters which are provided in the optical path of said two components of light for determining the shorter limit of the range of the spectroscopic distributions.

5. A meter for measuring the chlorophyll as defined in claim 3 or 4 wherein said photosensor for measuring the first component is a GaAsP-based photodiode, and said photosensor for measuring the second component is a silicon photodiode.

6. A meter for measuring the chlorophyll as defined in claim 3 wherein said spectroscopic optical element is a dichroic filter mirror.

* * * * *